(12) United States Patent
Opolski (10) Patent No.: US 7,226,466 B2
(45) Date of Patent: Jun. 5, 2007

(54) FLEXIBLE DELIVERY SYSTEM

(75) Inventor: Steve Opolski, Carlisle, MA (US)

(73) Assignee: NMT Medical, Inc., Boston, MA (US)

( * ) Notice: Subject to any disclaimer, the term of this patent is extended or adjusted under 35 U.S.C. 154(b) by 772 days.

(21) Appl. No.: 10/236,592

(22) Filed: Sep. 6, 2002

(65) Prior Publication Data

US 2003/0045901 A1 Mar. 6, 2003

Related U.S. Application Data

(60) Provisional application No. 60/317,117, filed on Sep. 6, 2001.

(51) Int. Cl.
*A61B 17/50* (2006.01)
*A61F 2/02* (2006.01)

(52) U.S. Cl. .................... 606/213; 623/23.72

(58) Field of Classification Search ................ 606/213
See application file for complete search history.

(56) References Cited

U.S. PATENT DOCUMENTS

| | | | |
|---|---|---|---|
| 3,874,388 A | 4/1975 | King et al. ............. 128/334 R |
| 4,007,743 A | 2/1977 | Blake ...................... 128/334 R |
| 4,800,890 A | 1/1989 | Cramer ........................ 128/657 |
| 4,836,204 A | 6/1989 | Landymore et al. .... 128/334 R |
| 4,932,419 A * | 6/1990 | de Toledo .................... 600/585 |
| 4,985,014 A | 1/1991 | Orejola ........................ 600/16 |
| 5,003,990 A * | 4/1991 | Osypka ....................... 600/585 |
| 5,025,799 A * | 6/1991 | Wilson ........................ 600/585 |
| 5,030,199 A | 7/1991 | Barwick et al. .............. 600/29 |
| 5,041,129 A | 8/1991 | Hayhurst et al. ............ 606/232 |
| 5,042,976 A | 8/1991 | Ishitsu et al. .................. 604/96 |
| 5,052,404 A * | 10/1991 | Hodgson ..................... 600/585 |
| 5,057,114 A | 10/1991 | Wittich et al. .............. 606/127 |
| 5,073,166 A | 12/1991 | Parks et al. .................... 609/93 |
| 5,108,420 A | 4/1992 | Marks ......................... 606/213 |
| 5,112,310 A | 5/1992 | Grobe ......................... 604/175 |
| 5,163,445 A * | 11/1992 | Christian et al. ........... 607/116 |
| 5,165,421 A | 11/1992 | Fleischhacker et al. ..... 128/772 |

(Continued)

FOREIGN PATENT DOCUMENTS

EP 1222897 7/2002

(Continued)

OTHER PUBLICATIONS

"Elastic Deployment," SMST-2000 Proceedings of the International Conference on Shape Memory and Superelastic Technologies, Apr. 30 to May 4, 2000, Asilomar Conference Center, 3 pages.

(Continued)

*Primary Examiner*—Michael J. Hayes
(74) *Attorney, Agent, or Firm*—Kirkpatrick & Lockhart Nicholson Graham LLP (57) ABSTRACT

A delivery system for implanting medical devices within a lumen or body cavity of a patient, the delivery system having a wire formed from a plurality of layered strands yielding a reduced bending stiffness for improved maneuverability with no reduction in overall tensile strength compared to delivery systems using a single wire and of comparable diameter. The physical properties of the delivery system permit optimal placement and retrieval of an intracardiac occluder within a patient.

17 Claims, 9 Drawing Sheets

U.S. PATENT DOCUMENTS

| | | | |
|---|---|---|---|
| 5,190,528 A | 3/1993 | Fonger et al. | 604/171 |
| 5,192,301 A | 3/1993 | Kamiya et al. | 606/213 |
| 5,284,488 A | 2/1994 | Sideris | 606/213 |
| 5,308,324 A * | 5/1994 | Hammerslag et al. | 604/528 |
| 5,312,341 A | 5/1994 | Turi | 604/96 |
| 5,333,625 A | 8/1994 | Klein | 128/898 |
| 5,334,217 A | 8/1994 | Das | 606/213 |
| 5,357,979 A | 10/1994 | Imran | 128/772 |
| 5,372,587 A | 12/1994 | Hammerslag et al. | 604/95 |
| 5,403,338 A | 4/1995 | Milo | 606/184 |
| 5,425,744 A | 6/1995 | Fagan et al. | 606/213 |
| 5,433,727 A | 7/1995 | Sideris | 606/213 |
| 5,451,235 A | 9/1995 | Lock et al. | 606/213 |
| 5,507,811 A | 4/1996 | Koike et al. | 623/11 |
| 5,540,712 A | 7/1996 | Kleshinski et al. | 606/198 |
| 5,545,138 A | 8/1996 | Fugoso et al. | 604/102 |
| 5,577,299 A | 11/1996 | Thompson et al. | 24/131 C |
| 5,578,045 A | 11/1996 | Das | 606/151 |
| 5,620,461 A | 4/1997 | Muijs Van De Moer et al. | 606/213 |
| 5,634,936 A | 6/1997 | Linden et al. | 606/213 |
| 5,683,411 A | 11/1997 | Kavteladze et al. | 606/200 |
| 5,700,252 A | 12/1997 | Klingenstein | 604/280 |
| 5,702,421 A | 12/1997 | Schneidt | 606/213 |
| 5,709,707 A | 1/1998 | Lock et al. | 606/213 |
| 5,720,300 A | 2/1998 | Fagan et al. | 128/772 |
| 5,720,754 A | 2/1998 | Middleman et al. | 606/127 |
| 5,725,552 A | 3/1998 | Kotula et al. | 606/213 |
| 5,733,294 A | 3/1998 | Forber et al. | 606/151 |
| 5,741,297 A | 4/1998 | Simon | 606/213 |
| 5,746,765 A | 5/1998 | Kleshinski et al. | 606/198 |
| 5,776,162 A | 7/1998 | Kleshinski | 606/198 |
| 5,800,516 A | 9/1998 | Fine et al. | 623/1 |
| 5,810,884 A | 9/1998 | Kim | 606/213 |
| 5,853,422 A | 12/1998 | Huebsch et al. | 606/213 |
| 5,861,003 A | 1/1999 | Latson et al. | 606/213 |
| 5,868,753 A | 2/1999 | Schatz | 606/108 |
| 5,879,366 A | 3/1999 | Shaw et al. | 606/213 |
| 5,895,404 A | 4/1999 | Ruiz | 606/185 |
| 5,902,317 A | 5/1999 | Kleshinski et al. | 606/198 |
| 5,904,703 A | 5/1999 | Gilson | 606/213 |
| 5,919,200 A | 7/1999 | Stambaugh et al. | 606/159 |
| 5,928,250 A | 7/1999 | Koike et al. | 606/139 |
| 5,944,738 A | 8/1999 | Amplatz et al. | 606/213 |
| 5,976,174 A | 11/1999 | Ruiz | 606/213 |
| 5,993,475 A | 11/1999 | Lin et al. | 606/213 |
| 6,007,558 A | 12/1999 | Ravenscroft et al. | 606/200 |
| 6,019,736 A * | 2/2000 | Avellanet et al. | 600/585 |
| 6,019,737 A | 2/2000 | Murata | 600/585 |
| 6,024,756 A | 2/2000 | Huebsch et al. | 606/213 |
| 6,030,007 A | 2/2000 | Bassily et al. | 289/1.5 |
| 6,030,405 A | 2/2000 | Zarbatany et al. | 606/191 |
| 6,056,760 A | 5/2000 | Koike et al. | 606/148 |
| 6,077,291 A | 6/2000 | Das | 606/213 |
| 6,080,182 A * | 6/2000 | Shaw et al. | 606/213 |
| 6,086,610 A | 7/2000 | Duerig et al. | 623/1 |
| 6,113,609 A | 9/2000 | Adams | 606/139 |
| 6,117,159 A | 9/2000 | Huebsch et al. | 606/213 |
| 6,129,755 A | 10/2000 | Mathis et al. | 623/1.15 |
| 6,139,572 A | 10/2000 | Campbell et al. | 623/1.11 |
| 6,142,975 A | 11/2000 | Jalisi et al. | 604/170.1 |
| 6,149,664 A | 11/2000 | Kurz | 606/194 |
| 6,171,329 B1 | 1/2001 | Shaw et al. | 606/213 |
| 6,174,322 B1 | 1/2001 | Schneidt | 606/213 |
| 6,191,365 B1 * | 2/2001 | Avellanet | 174/128.1 |
| 6,206,907 B1 * | 3/2001 | Marino et al. | 606/215 |
| 6,214,029 B1 | 4/2001 | Thill et al. | 606/213 |
| 6,221,092 B1 | 4/2001 | Koike et al. | 606/213 |
| 6,234,981 B1 | 5/2001 | Howland | 600/585 |
| 6,254,550 B1 | 7/2001 | McNamara et al. | 600/585 |
| 6,270,515 B1 | 8/2001 | Linden et al. | 606/213 |
| 6,280,539 B1 * | 8/2001 | Abrams et al. | 148/402 |
| 6,290,674 B1 | 9/2001 | Roue et al. | 604/107 |
| 6,306,105 B1 | 10/2001 | Rooney et al. | 600/585 |
| 6,312,446 B1 | 11/2001 | Huebsch et al. | 606/213 |
| 6,322,548 B1 | 11/2001 | Payne et al. | 604/500 |
| 6,342,064 B1 | 1/2002 | Koike et al. | 606/213 |
| 6,346,074 B1 | 2/2002 | Roth | 600/121 |
| 6,348,041 B1 | 2/2002 | Klint | 600/585 |
| 6,352,531 B1 | 3/2002 | O'Connor et al. | 606/15 |
| 6,352,561 B1 | 3/2002 | Leopold et al. | 623/123 |
| 6,355,052 B1 | 3/2002 | Neuss et al. | 606/213 |
| 6,375,671 B1 | 4/2002 | Kobayashi et al. | 606/213 |
| 6,379,368 B1 | 4/2002 | Corcoran et al. | 606/153 |
| 6,383,146 B1 | 5/2002 | Klint | 600/585 |
| 6,387,060 B1 | 5/2002 | Jalisi | 600/585 |
| 6,387,104 B1 | 5/2002 | Pugsley, Jr. et al. | 606/139 |
| 6,402,772 B1 | 6/2002 | Amplatz et al. | 606/200 |
| 6,440,152 B1 | 8/2002 | Gainor et al. | 606/213 |
| 6,482,224 B1 | 11/2002 | Michler et al. | 606/219 |
| 6,494,888 B1 | 12/2002 | Laufer et al. | 606/153 |
| 6,551,344 B2 | 4/2003 | Thill | 606/213 |
| 6,596,013 B2 | 7/2003 | Yang et al. | 606/215 |
| 6,623,508 B2 | 9/2003 | Shaw et al. | 606/213 |
| 6,623,518 B2 | 9/2003 | Thompson et al. | 623/1.11 |
| 2001/0021831 A1 * | 9/2001 | Fleischhacker et al. | 604/264 |
| 2001/0037129 A1 | 11/2001 | Thill | 606/213 |
| 2002/0010481 A1 | 1/2002 | Jayaraman et al. | 606/151 |
| 2002/0019648 A1 | 2/2002 | Akerfeldt et al. | 606/213 |
| 2002/0026208 A1 | 2/2002 | Roe et al. | 606/190 |
| 2002/0052572 A1 | 5/2002 | Franco et al. | 604/8 |
| 2002/0077555 A1 | 6/2002 | Schwartz | 600/486 |
| 2002/0096183 A1 | 7/2002 | Stevens et al. | 128/898 |
| 2002/0099389 A1 | 7/2002 | Michler et al. | 606/139 |
| 2002/0107531 A1 | 8/2002 | Schreck et al. | 606/142 |
| 2002/0120323 A1 | 8/2002 | Thompson et al. | 623/1.11 |
| 2002/0128680 A1 | 9/2002 | Pavlovic | 606/200 |
| 2002/0183786 A1 * | 12/2002 | Girton | 606/213 |
| 2002/0183787 A1 | 12/2002 | Wahr et al. | 606/213 |
| 2003/0028213 A1 | 2/2003 | Thill et al. | 606/200 |
| 2003/0045893 A1 | 3/2003 | Ginn | 606/151 |
| 2003/0050665 A1 | 3/2003 | Ginn | 606/215 |
| 2003/0059640 A1 | 3/2003 | Marton et al. | 428/544 |
| 2003/0100920 A1 | 5/2003 | Akin et al. | 606/213 |
| 2003/0139819 A1 | 7/2003 | Beer et al. | 623/23 |
| 2003/0195530 A1 | 10/2003 | Thill | 606/151 |
| 2003/0208232 A1 | 11/2003 | Blaeser et al. | 606/213 |

FOREIGN PATENT DOCUMENTS

| | | |
|---|---|---|
| WO | WO 98/07375 | 2/1998 |
| WO | WO 99/18862 | 4/1999 |
| WO | WO 99/18864 | 4/1999 |
| WO | WO 99/18870 | 4/1999 |
| WO | WO 99/18871 | 4/1999 |
| WO | WO 01/78596 | 10/2001 |
| WO | WO 03/077733 A2 | 9/2003 |

OTHER PUBLICATIONS

"Trans-septal Catheterization for Radiofrequency Catheter Ablation of Cardiac Arrhythmias. Results and Safety of a Simplified Method," by R. De Ponti, et al., European Heart Journal, vol. 19, Jun. 1998, pp. 943-950.

"The Puncture Needle as Guidewire: Needle Guide Technique for Percutaneous Nephrostomy," by Irvin F. Hawkins, Jr., M.D., et al., Seminars in Interventional Radiology, vol. 4, No. 2, Jun. 1987, pp. 126-130.

"PFO and Stroke: The Hidden Connection," by Paul Kramer, MD, Endovascular Today, http://www.endovasculartoday.com/02_current/10.html, printed Oct. 9, 2003.

"The Puncture Technique: A New Method of Transcatheter Closure of Patent Foramen Ovale," by Carlos E. Ruiz, M.D., Ph.D., et al., Catheterization and Cardiovascular Interventions, vol. 53, 2001, pp. 369-372.

"New Transseptal Puncture Technique for Transcatheter Closure of Patent Foramen Ovale," by Robert J. Sommer, M.D., et al., Mount Sinai Medical Center, New York, New York, publication date unknown but believed to be Jun. 2002 or earlier.

Patent Cooperation Treaty (PCT) International Search Report (PCT Article 18 and Rules 43 and 44), International Application No. PCT/US02/28405, International Filing Date: Jun. 9, 2002, Applicant: NMT Medical, Inc.

* cited by examiner

FLEXIBLE DELIVERY SYSTEM

RELATED APPLICATION

This application claims the benefit of U.S. Provisional Application No. 60/317,117, filed Sep. 6, 2001, the entire disclosure of which is hereby incorporated by reference.

FIELD OF THE INVENTION

This invention generally relates to a delivery system for a medical device. More particularly, this invention relates to a system for the delivery and retrieval of a prosthetic occluder in the cardiovascular system of a patient.

DESCRIPTION OF THE RELATED ART

Numerous systems for percutaneous catheter delivery of implants have been devised over the years in order to assist physicians in delivering and positioning implants within the human body in a minimally invasive manner. A classic problem with many of these percutaneous delivery systems is that they can often adversely effect the position of the device that is being implanted. Many devices are released in stages and consequently, if the position of the device is not acceptable, the device can be removed or repositioned. If the delivery system, however, adversely influences the positioning of the implant, the physician is forced to estimate the effect of this on the implant position and take such effect into consideration when assessing final implant position prior to release. The final released position of the implant may be different from its position when still attached to the delivery system. Additionally, the movement of the implant that occurs following release from the delivery system can adversely effect the final position resulting in a less desirable final result (such as a residual leak in the case of septal occluders) or even embolization of the implant device.

Modern medical technology has produced a number of medical devices which are designed for compression into a small size tube or catheter to facilitate introduction into the vasculature and which are subsequently expandable for either occlusion of defects or holes in the heart, such as septal occluders (discussed in more detail below), or which contact the walls of the passageway or blood vessel, in the case of vena cava filters or stents. Among these devices are septal occluders such as the occluder shown in U.S. Pat. No. 5,425,744, the entire disclosure of which is hereby incorporated by reference. While the occluder noted above is a permanent implant which, when implanted is designed to remain in place, it can be recovered at a variety of stages during the implantation procedure. The most critical stage is following implant deployment but prior to release from the delivery system. To date, ball to ball (or pin to pin) attach/release mechanisms have been employed to implant and position such septal occluders within the heart.

Either congenitally or by acquisition, abnormal openings, holes or shunts can occur between the chambers of the heart or the great vessels, causing shunting of blood through the opening. These holes or shunts may develop between the left and right atria along the muscular wall which separates the two: the interatrial septum, a wall between the right and left ventricles which are separated by the interventricular septum. Such deformities are usually congenital and result from the incomplete formation of the septum, or wall, between chambers during fetal life when the heart forms from a folded tube into a four chambered, two unit system. These deformities can cause significant problems. Ultimately, the ill effects of these defects cause added strain on the heart which may result in heart failure if the defects are not corrected. One such defect, a patent foramen ovale (PFO), is a persistent, one-way, usually flap-like opening in the wall between the right atrium and left atrium of the heart. Since left atrial (LA) pressure is normally higher than right atrial (RA) pressure, the flap typically stays closed. Under certain conditions, however, RA pressure can exceed LA pressure creating the possibility for right to left shunting that can allow blood clots to enter the systemic circulation. This is of particular importance with patients who are prone to forming venous thrombus such as those with deep vein thrombosis or clotting abnormalities.

Nonsurgical (percutaneous) closure of PFOs has become possible using a variety of mechanical closure devices, allowing patients to avoid the potential side effects often associated with standard anticoagulation therapies or surgery. An example of an intracardiac medical implant is provided herein. Generally, these devices typically consist of a metallic structural framework combined with a synthetic tissue scaffold material. Similar intracardiac defects also currently treated with such devices include atrial septal defects (ASDs), ventricular septal defects (VSDs), and, left atrial appendages (LAAs). While standard synthetic tissue scaffolds are quite effective in most ASD and VSD indications, such thrombogenicity can be disastrous in both the PFO and the left atrial appendage (LAA) indications.

Unlike many other implantable medical devices, intracardiac occluders present special challenges for a medical device delivery system. First, the occluder must be very carefully and precisely deployed within the of the center defect to assure proper closure. Second, the tortuous anatomy of the heart and vascular system necessitate a delivery system capable of traversing the small radii of curvature and the confines of the heat chambers for delivery of the occluder to the deployment site.

Typical delivery systems for medical implant devices such as a septal occluder must satisfy a number of requirements to be effective. A common requirement is a predetermined tensile strength and stiffness in order for the delivery system to function properly. Often, at odds with this requirement for high tensile strength and stiffness, there is a need for bending flexibility so the delivery system can safely be guided to the intended target. Consequently, there is normally a design tradeoff in balancing these two needs. The delivery system may be required to be steerable through body lumens or cavities and be positionable or aimable with respect to organs or tissue within the body by an operator at a position external to the body. For example, a single 0.013 inch core wire imparts a significant stiffness to a device which reduces flexibility and can impede maneuverability through a body lumen or cavity.

Examples of delivery systems commonly in use within tortuous anatomy consist of an elongate spring type guide tube through which a single elongate core wire passes. A metal ball is formed on the distal end of the core wire. Delivery systems employing such spring type guide tubes require the use of a safety wire to keep the spring compressed when a tensile load is applied to the delivery system. Further, the use of spring type delivery systems generally require the use of separate guidewire catheters to help negotiate the implant to the deployment site. This requirement requires both the use of additional equipment and often taxes space limitations during a catherization procedure. The bending stiffness of the system formed by the spring guide and core wire is dominated by the relatively stiff core wire. Certain medical implant devices, such as intracardiac occluders, when implanted in a defect, may be required to remain attached to the delivery system for a period of time during which the clinician assesses the defect closure result.

SUMMARY OF THE INVENTION

A delivery system according to the present invention provides a device and method for implanting and removing medical devices. In one aspect, the invention relates to a medical device for implanting an intracardiac occluder within the heart of a patient. The medical device includes an elongate body member having a distal end and a proximal end and a longitudinal axis extending therethrough. The elongate body member includes a plurality of layered strands extending along the longitudinal axis. An attachment device is connected to the distal end of the elongate body member for releasable coupling to the intracardiac occluder. In one embodiment of the invention, the medical device includes a ball connected to the distal end of the elongate body member for releasable coupling to the intracardiac occluder. In another embodiment, the attachment device provides a pivoting connection between the implant and the delivery device in order to minimize any bending of the delivery device while inserting and positioning the implant. In a further embodiment of the invention, the medical device includes a catheter defining a lumen and that is slideably disposed along the longitudinal axis of the elongate body member. In various embodiments, the elongate body member includes multiple strands arranged in various configurations to provide the desired combination of material properties including high tensile strength and reduced bending stiffness.

This construction provides improved maneuverability in clinical applications with no reduction in overall tensile strength. High tensile strength is desirable in a medical delivery system for proper removal of a medical device from the body of a patient without elongation of one or more components of the device or breakage due to material failure. The physical properties of the delivery system may permit optimal placement and retrieval of medical devices including an intracardiac occluder within the heart of a patient.

In one embodiment, the strands of the medical device include stainless steel coated with a biocompatible material. In other embodiments strands include a nickel cobalt alloy.

It is an object of the invention to provide a delivery system having high tensile strength and low stiffness for implanting and removing medical devices.

It is another object of the invention is to provide a delivery system which retains the high tensile stiffness and strength required by its application while providing a significantly reduced bending stiffness relative to single core wire devices.

It is a further object of the invention to provide a delivery system for medical implant devices which replaces a single, elongate core wire with a wire rope formed from a plurality of layered strands.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

Delivery systems embodying the invention may include a wide variety of constructions. The delivery system according to the invention includes a plurality of helically layered strands providing reduced bending stiffness without compromising high tensile strength for delivery of a medical device to a body lumen or cavity. This combination of reduced bending stiffness and high tensile strength in a delivery system is advantageous when used with any medical implant, and particularly advantageous for implants requiring a tether, such as an intracardiac prosthetic occluder, either permanently or temporarily.

Embodiments of the present invention are described below. It is, however, expressly noted that the present invention is not limited to these embodiments, but rather the intention is that variations, modifications, and equivalents that are apparent to the person skilled in the art are also included.

Figure 1:
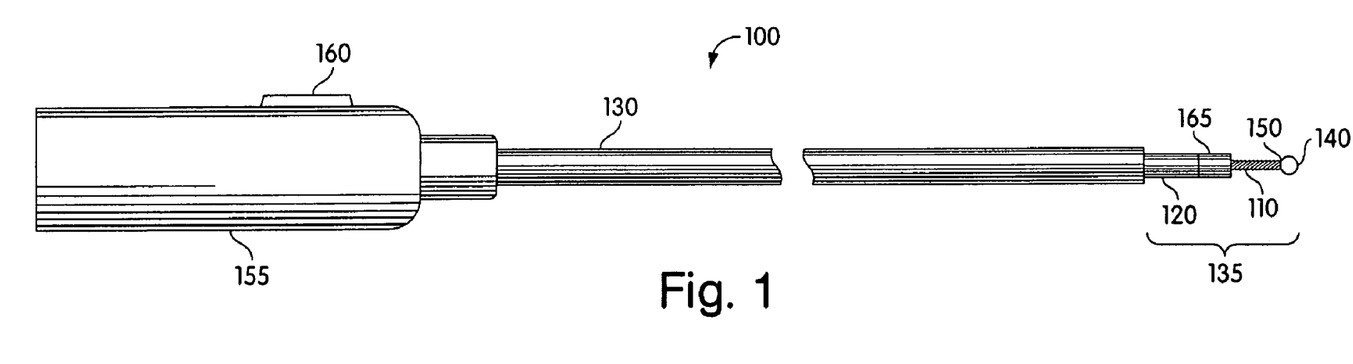
FIG. 1 depicts a schematic view of one embodiment of the flexible delivery system according to the invention.
Figure 2:
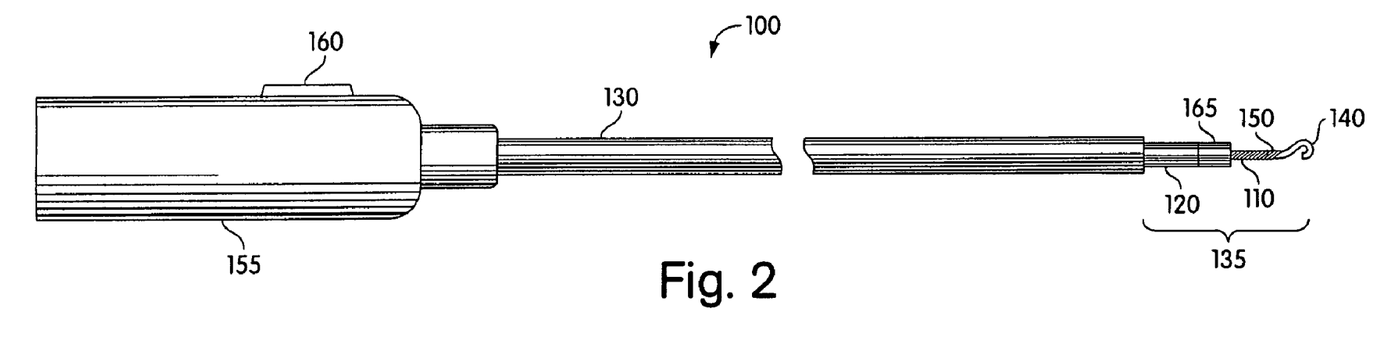
FIG. 2 depicts a schematic view of another embodiment of the flexible delivery system according to the invention.

FIGS. 1 and 2 show generally a delivery system 100 having a coaxial elongate construction extending along a longitudinal direction including a wire 110, substantially enclosed by a catheter 120, the catheter being substantially enclosed by a sheath 130. Located at a distal end 135 of the delivery system 100 is an attachment device 140 which, in the embodiment depicted in FIG. 1, comprises a ball 140, and in the embodiment depicted in FIG. 2, comprises an alternative embodiment of an attachment device 140, for example, a hook 140, either of which are coupled to the wire 110 at attachment point 150. Other attachment device configurations are contemplated and are not limited to those depicted in the illustrations. In one embodiment, the ball 140 depicted in FIG. 1 has a diameter between 0.0016 and 0.025 inches. There are a variety of ways to secure the attachment device to the wire 110, e.g., welding, adhering, and threading. The connection of the attachment device 140 to the wire 110, permits relative movement with respect to the catheter 120 via the handle 155 and actuator 160 located at a proximal end of the delivery system 100. The distal end 135 of the delivery system 100 may be coupled to a medical device, for example, a prosthetic occluder (not shown) and is capable of being advanced through the vascular system and into a heart chamber of a patient. The wire 110 typically has a length in the range of 10 to 140 inches and preferably between 20 and 120 inches. The wire 110 has an outside diameter in the range of 0.0008 to 0.042 inches. Translational movement of the actuator 160 and rotational movement of the handle 155 are communicated along the longitudinal length of the delivery system 100 to the distal end 135 for manipulation, delivery, implantation, and/or removal of the occluder from within the body of a patient.

Figure 3A:
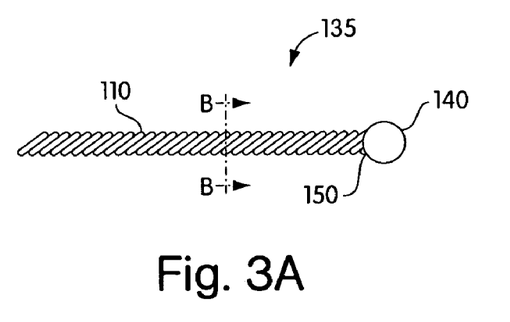
FIG. 3A depicts a schematic view of the distal end of the flexible delivery system of FIG. 1.
Figure 3B:
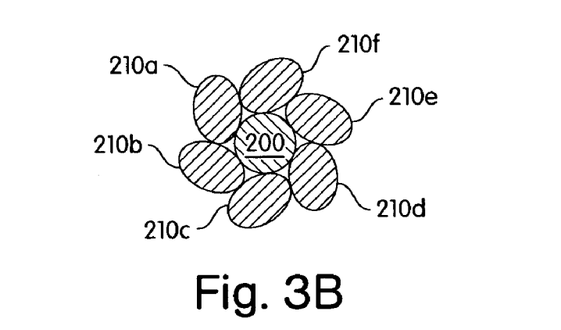
FIGS. 3B and 3C depict cross-sectional views of two embodiments of the flexible delivery system of FIG. 3A along section B-B.
Figure 3C:
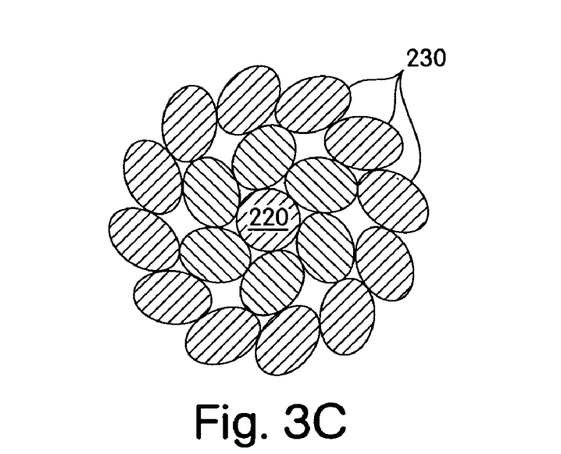

As shown in FIGS. 3A to 3C, the wire 110 is formed of a plurality of twisted strands. In one embodiment, shown in cross-section in FIG. 3B, the wire 110 is formed of 7 strands, each of which is approximately 0.005 inches in diameter. The strands may be formed of extruded filaments, twisted filaments, or braided filaments or any of their combination. In a particular embodiment, a central strand 200 is bounded by helically-wrapped outer strands 210a to 210f. The wire 110 may be formed by a plurality of strands in different patterns and include strands of different diameters. For example, FIG. 3C depicts an alternative embodiment wherein the wire 110 may be formed of nineteen twisted strands, each of which is approximately 0.003 inches in diameter. A central strand 220 is bounded by helically-wrapped outer strands 230. The wire 110 according to the invention may be designed to match the tensile stiffness of a single core wire while reducing the bending stiffness of a delivery system for a medical implant device.

Figure 4A:
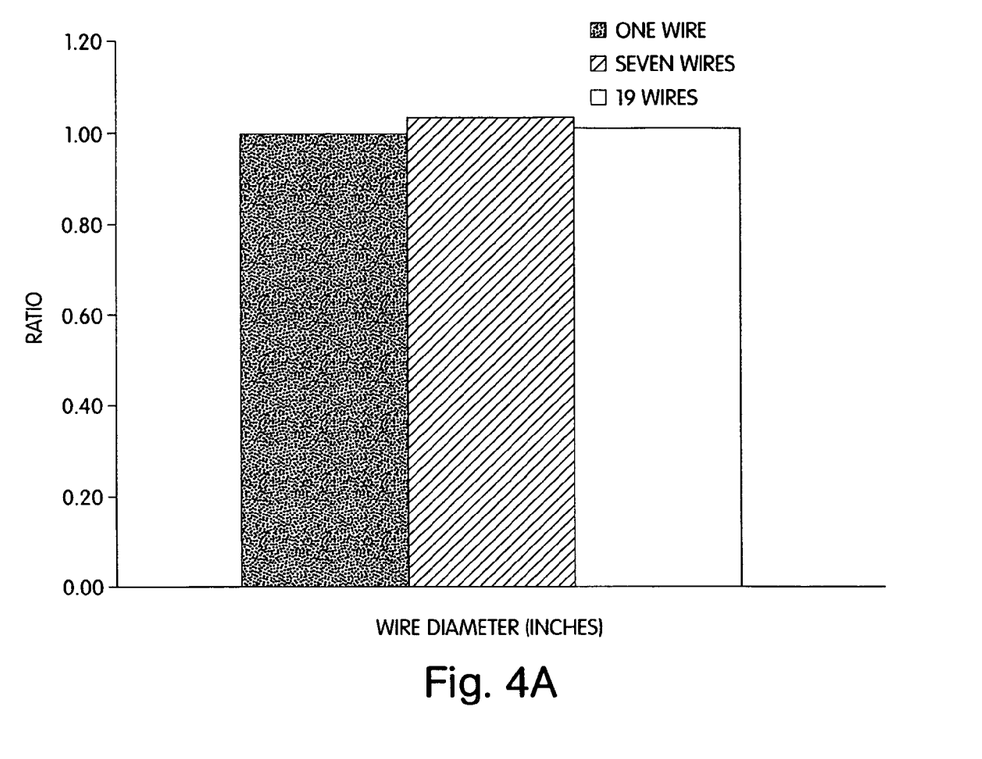
FIG. 4A graphically depicts the relationship between wire diameter and tensile stiffness for varying embodiments according to the invention.
Figure 4B:
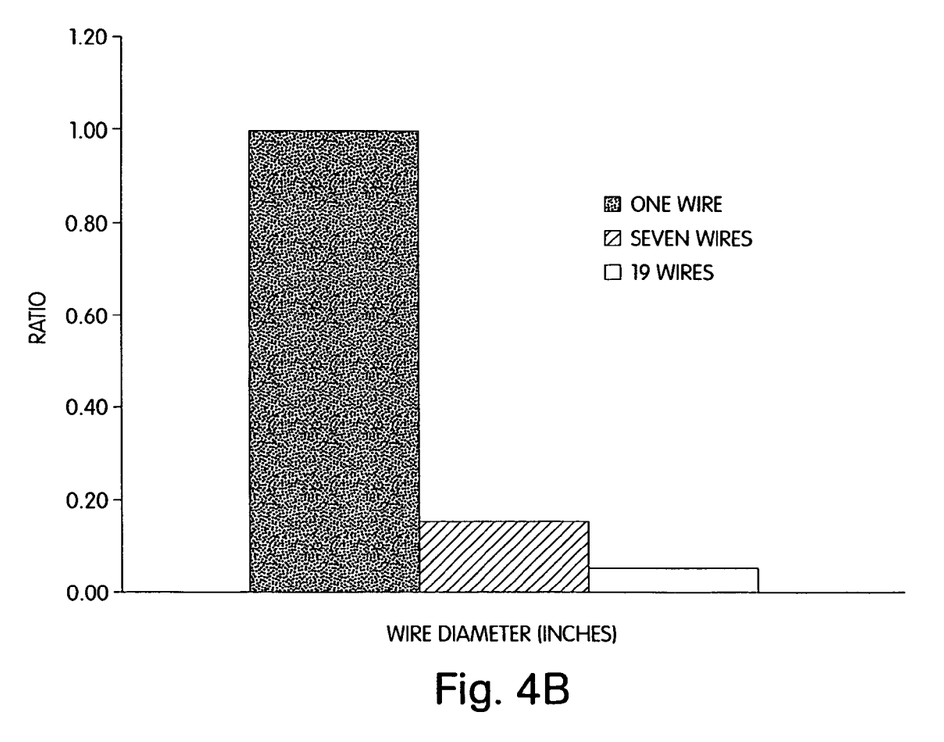
FIG. 4B graphically depicts the relationship between wire diameter and bending stiffness for varying embodiments according to the invention.

As shown graphically in FIGS. 4A and 4B, it has been found that when the wire 110 is formed from a plurality of 7 strands, as depicted in FIG. 3B, it has substantially the same tensile stiffness as one 0.013 inch single core wire, but only approximately 16 percent of the bending stiffness of the same single core wire. By replacing a single core wire with a plurality of strands having the same approximate aggregate diameter, the wire 110 is formed having all the tensile stiffness of the single core wire having a 0.013 inch outer diameter, but which is significantly more flexible than the single core wire. The helically bundled configuration determines that the outer diameter of a wire formed from a plurality of 7 strands is approximately 3 times the diameter of an individual strand. Moreover, the outer diameter of a wire formed from a plurality of nineteen strands is approximately 5 times the diameter of an individual strand.

Figure 5:
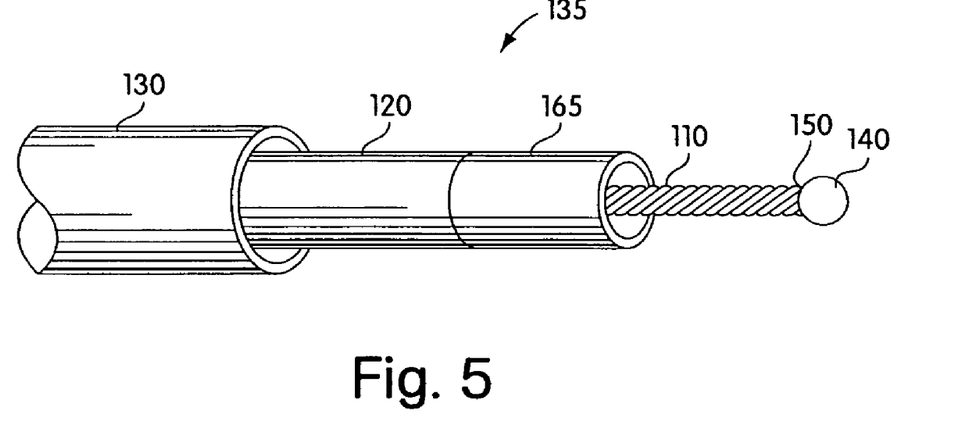
FIG. 5 depicts a detailed perspective view of the distal end of the embodiment of the flexible delivery system depicted in FIG. 1.

FIG. 5 depicts a detailed perspective view of the distal end 135 of the delivery system 100. Relative movement between the wire 110 and the catheter 120 permits coupling and decoupling of a medical device. The catheter 120 is moveable with respect to the wire 110 and the ball 140 attached thereto, and the sheath 130 is moveable with respect to the catheter 120. Alternatively, the wire 110 and the ball attached thereto is moveable with respect to the catheter 120. A distal sleeve 165 is attached to the distal end 135 of the catheter 120. In one embodiment, the distal sleeve 165 is comprised of stainless steel and has a diameter of about 2 to 3 times the diameter of the ball 140.

Figure 6A:
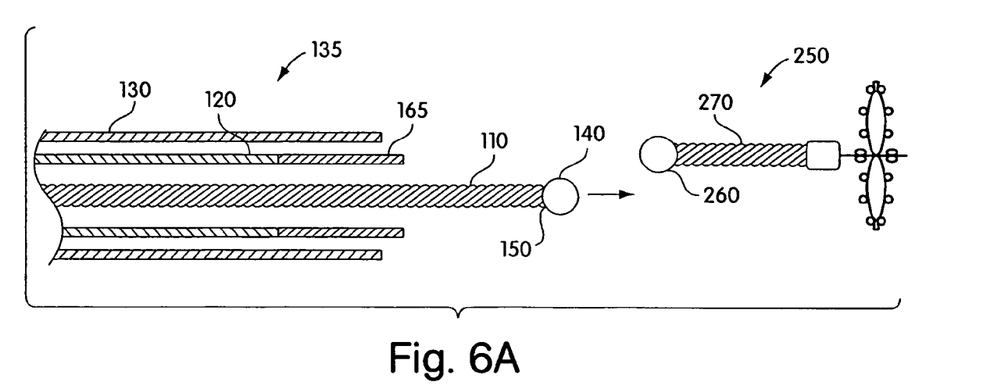
FIGS. 6A to 6C depict longitudinal cross-sectional views of the distal end of the embodiment of the flexible delivery system of depicted in FIG. 1.
Figure 6B:
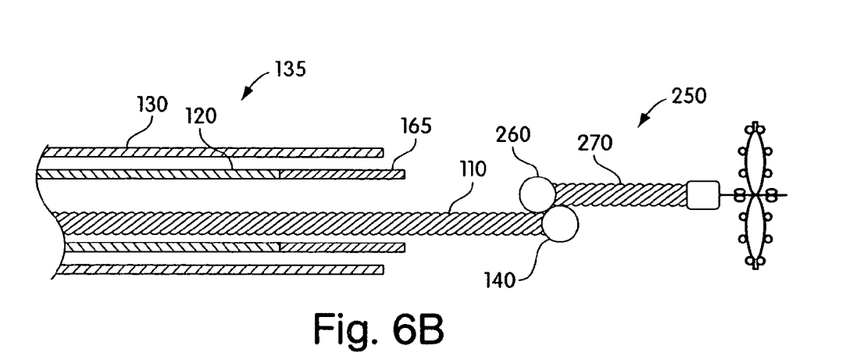
Figure 6C:
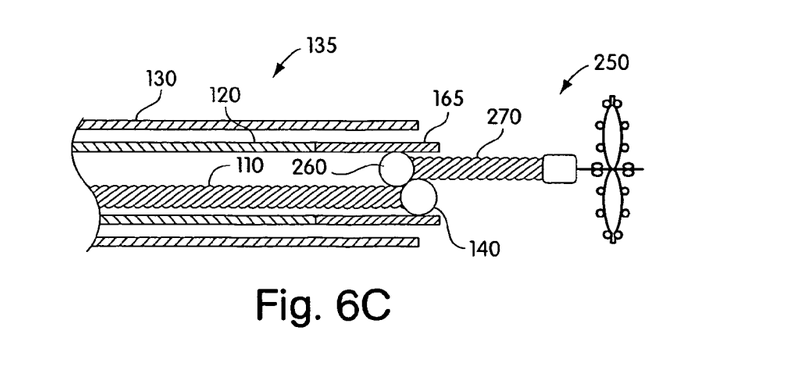
Figure 7A:
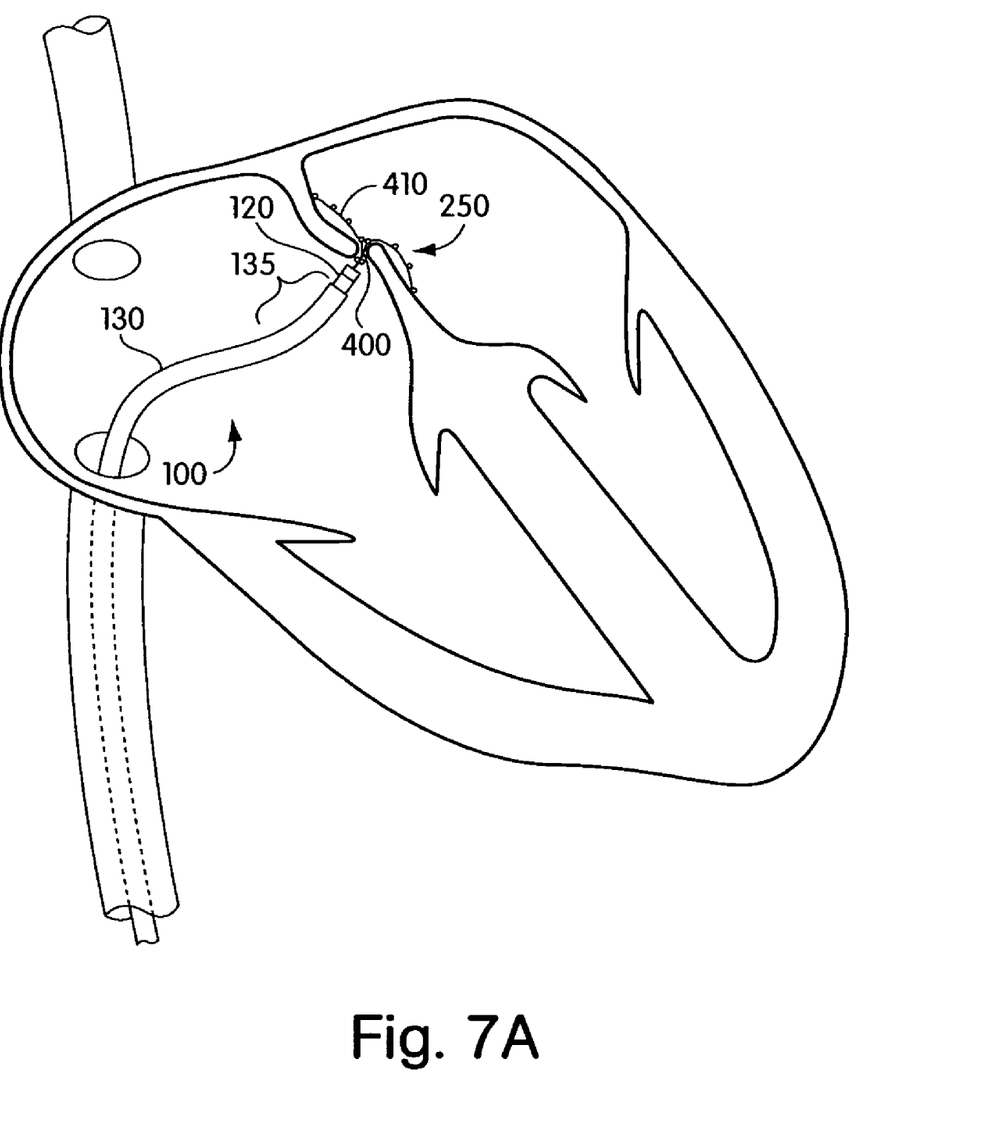
FIGS. 7A to 7C depict a clinical application of the embodiment of the flexible delivery system depicted in FIG. 1.
Figure 7B:
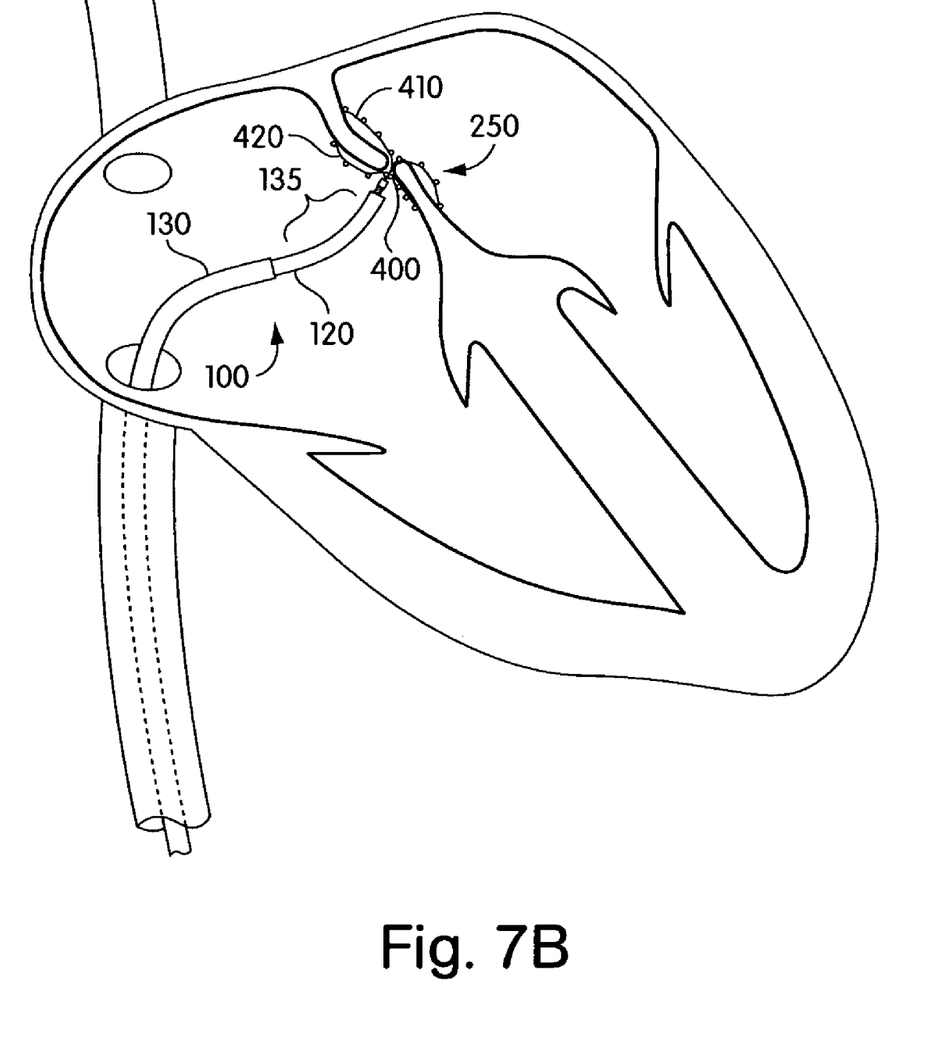
Figure 7C:
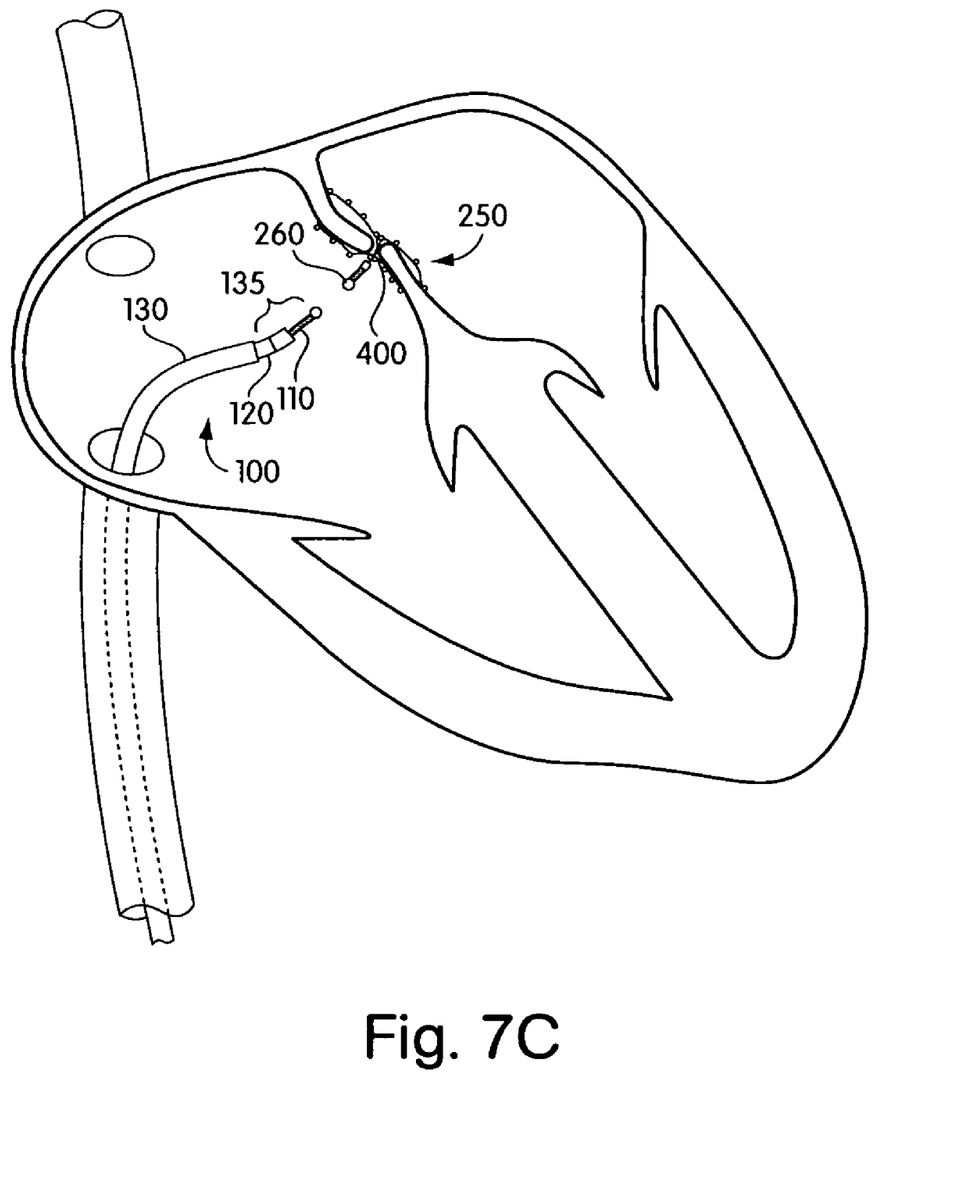

FIGS. 6A to 6C schematically depict the distal end 135 of the delivery system 100 including the wire 110 engaging and coupling a prosthetic occluder 250. A ball 260 similar to the ball 140 of the delivery system is connected to the occluder 250 by the linkage 270. The occluder 250 is attached to the distal end 135 of the delivery system 100 as follows. The ball 140 of the delivery system 100 is placed proximate to the ball 260 of the occluder 250 such that the ball 140 is adjacent but located longitudinally distal to the ball 260. The catheter 120 is moved relative to the wire 110 toward the ball 140 as shown in FIG. 6B. The catheter is slid over both the ball 140 of the delivery system 100 and the ball 260 of the occluder, locking ball 140 and 260 together and within the inner diameter of the catheter 120, thereby preventing longitudinal movement of the occluder 250 as shown in FIG. 6C. In this way, the occluder 250 may be releasable secured to the distal end 135 of the delivery device during implantation of the occluder 250 within the patient. The distal sleeve 165 provides the catheter 135 with sufficient hoop strength for coupling the ball 140 of the wire 110 to the ball 260 of the occluder 250 within the catheter 120. After implantation, the delivery system 100 may remain tethered to the occluder 250 at the ball-to-ball connection to permit the clinician to asses the closure result. After the occluder 250 is coupled to the delivery system 100 via the connection of ball 140 to ball 260, the low bending stiffness of the wire 110 facilitates improved maneuverability of the occluder 250 for insertion, positioning, and implantation within the vascular system of a patient. The high tensile strength of the wire 110 enables removal of the occluder 250 while minimizing elongation of the delivery system 100 and the risk of failure to breakage The general deployment of the septal occluder 250 in a clinical application is depicted schematically in FIGS. 7A to 7C. The distal end 135 of the delivery system 100 including the wire 110 according to the invention is positioned proximate to a wall defect 400 in the heart. As shown in FIG. 7A, a distal sealing membrane 410 of the occluder 250 is extracted out of the catheter 120 permitting the distal sealing membrane 410 to expand to the deployed shape. As shown in FIG. 7B, the distal end 135 of the delivery system 100 is withdrawn away from the wall defect 400, the occluder 250 is further extracted out of the catheter 120, permitting the proximal sealing membrane 420 to expand to the deployed shape. As shown in FIG. 7C, when the occluder 250 is properly positioned, the catheter 120 is retracted from the attachment mechanism (as shown in FIGS. 6A to 6C) and the ball 260 disengages from the distal end 135 of the delivery system 100 thereby releasing the occluder 250, now implanted in a wall of the heart. The schematic depiction of the human heart, the chambers therein, and the surrounding vascular system demonstrate the tortuous anatomy necessitating the low bending stiffness provided by the wire 110 of the delivery system 100. As the representative curvature of the distal end 135 of the delivery system 100 shows, the low bending stiffness of the wire 110 permits improved maneuverability of the delivery system 100, and minimizes any adverse effect the delivery system 100 may have on the final position of the occluder 250 within the wall defect 400.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A medical device for implanting an intracardiac occluder within the heart of a patient, the device comprising:
   a sheath comprising a lumen;
   a locking catheter defining a lumen comprising a proximal end and a distal end, said locking catheter longitudinally disposed in the lumen of the sheath;
   an elongate body member extending from a proximal end to a distal end and comprising a plurality of twisted layered strands extending along the longitudinal axis of the elongate body member; and an attachment device connected to the distal end of the elongate body member for releasable coupling to the intracardiac occluder, wherein said distal lumen of said locking catheter is dimensioned to releasably receive said attachment device and a complementary locking mechanism connected to the intracardiac occluder, said locking catheter slideably disposed along the longitudinal axis of the elongate body member for releasably coupling the locking mechanism on the intracardiac occcluder to the attachment device on the distal end of the elongate body member.

2. The medical device of claim 1, wherein the attachment device comprises a ball connected to the distal end of the elongate body member for releasable coupling to the intracardiac occluder.

3. The medical device of claim 1, wherein the strands extending along the longitudinal axis are arranged in a helix.

4. The medical device of claim 3 wherein the elongate body member comprises 7 strands.

5. The medical device of claim 3 wherein the elongate body member comprises nineteen strands.

6. The medical device according to claim 1, wherein the elongate body member comprises stainless steel coated with a biocompatible material.

7. The medical device according to claim 1, wherein the elongate body member comprises nickel cobalt alloy.

8. The medical device of claim 1 wherein the elongate body member further comprises a central strand bound by the plurality of twisted layered strands.

9. A device for implanting a medical device within a patient, the device comprising:

an elongate body member extending along a longitudinal axis and having a distal end and a proximal end;

the elongate body member comprising a plurality of helically layered strands having substantially the same diameter;

an attachment device connected to the distal end of the elongate body member for releasable coupling to the medical device; and a means for releasably coupling the attachment device to the distal end of the elongate body member.

10. The medical device of claim 9, further comprising a catheter defining a lumen and slideably disposed along the longitudinal axis of the elongate body member.

11. The medical device according to claim 9 wherein each strand comprises a diameter of approximately 0.005 inches.

12. The medical device according to claim 9 wherein each strand comprises a diameter of approximately 0.003 inches.

13. The medical device according to claim 9, wherein the elongate body member comprises stainless steel coated with a biocompatible material.

14. The medical device according to claim 9, wherein the elongate body member comprises nickel cobalt alloy.

15. The medical device of claim 9 wherein the elongate body member further comprises a central strand bound by the plurality of helically layered strands.

16. A method for delivering an intracardiac occluder to the heart of a patient, the method comprising the steps of:

a. providing a medical device comprising:

an elongate body member defining a lumen and comprising a plurality of twisted layered strands extending along a longitudinal axis in the lumen and having a distal end and a proximal end, and an attachment device coupled to the distal end of the elongate body member for releasable connection to the intracardiac occluder;

b. introducing the intracardiac occluder into the heart of the patient proximate to the location of the defect;

c. centering the intracardiac occluder across the defect;

d. implanting the intracardiac occluder within the defect;

e. detaching the intracardiac occluder from the distal end of the medical device; and f. withdrawing the medical device from the heart of the patient.

17. The method of claim 16 wherein the elongate body member further comprises a central strand bound by the plurality of twisted layered strands.

* * * * *